(12) United States Patent
Lee

(10) Patent No.: US 6,442,432 B2
(45) Date of Patent: Aug. 27, 2002

(54) INSTRUMENTATION AND SOFTWARE FOR REMOTE MONITORING AND PROGRAMMING OF IMPLANTABLE MEDICAL DEVICES (IMDS)

(75) Inventor: Michael Thomas Lee, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/745,038

(22) Filed: Dec. 20, 2000

Related U.S. Application Data
(60) Provisional application No. 60/173,080, filed on Dec. 24, 1999.

(51) Int. Cl.$^7$ ................................ A61N 5/00
(52) U.S. Cl. ...................................... 607/59
(58) Field of Search ...................... 607/59, 32

(56) References Cited

U.S. PATENT DOCUMENTS

| | | | |
|---|---|---|---|
| 5,544,661 A | 8/1996 | Davis et al. | 128/700 |
| 5,593,426 A | 1/1997 | Morgan et al. | 607/5 |
| 5,626,630 A | 5/1997 | Markowitz et al. | 607/60 |
| 5,640,953 A | 6/1997 | Bishop et al. | 128/630 |
| 5,720,770 A | 2/1998 | Nappholz et al. | 607/30 |
| 5,752,976 A | 5/1998 | Duffin et al. | 607/32 |
| 5,782,878 A | 7/1998 | Morgan et al. | 607/5 |
| 5,857,967 A | 1/1999 | Frid et al. | 600/301 |
| 5,897,493 A | 4/1999 | Brown | 600/300 |
| 5,987,519 A | 11/1999 | Peifer et al. | 709/230 |
| 5,997,476 A | 12/1999 | Brown | 600/300 |
| 6,004,276 A | 12/1999 | Wright et al. | 600/508 |
| 6,038,469 A | 3/2000 | Karlsson et al. | 600/512 |
| 6,093,146 A | 7/2000 | Filangeri | 600/300 |
| 6,141,584 A | 10/2000 | Rockwell et al. | 607/5 |
| 6,168,563 B1 | 1/2001 | Brown | 600/301 |
| 6,183,417 B1 | 2/2001 | Geheb et al. | 600/301 |

*Primary Examiner*—Scott M. Getzow
(74) *Attorney, Agent, or Firm*—Girma Wolde-Michael

(57) ABSTRACT

A data communication system is provided which permits collaboration between distributed clinicians regarding distributed or remote implantable medical devices (IMDs). A central computing resource capable of storing and distributing patient device and clinician location and contact data is provided, as well as a network providing communication with the computing resource. A deployed IMD may be polled by an interface device external to the host patient, and data may be transmitted to the interface device by wireless communication. This data may be transmitted to a central computer for storage and distribution. The data may be distributed to various clinicians in communication with the central computer. These clinicians may use this information, either directly or indirectly, to contact remote clinicians and medical devices in communication with the network.

53 Claims, 2 Drawing Sheets

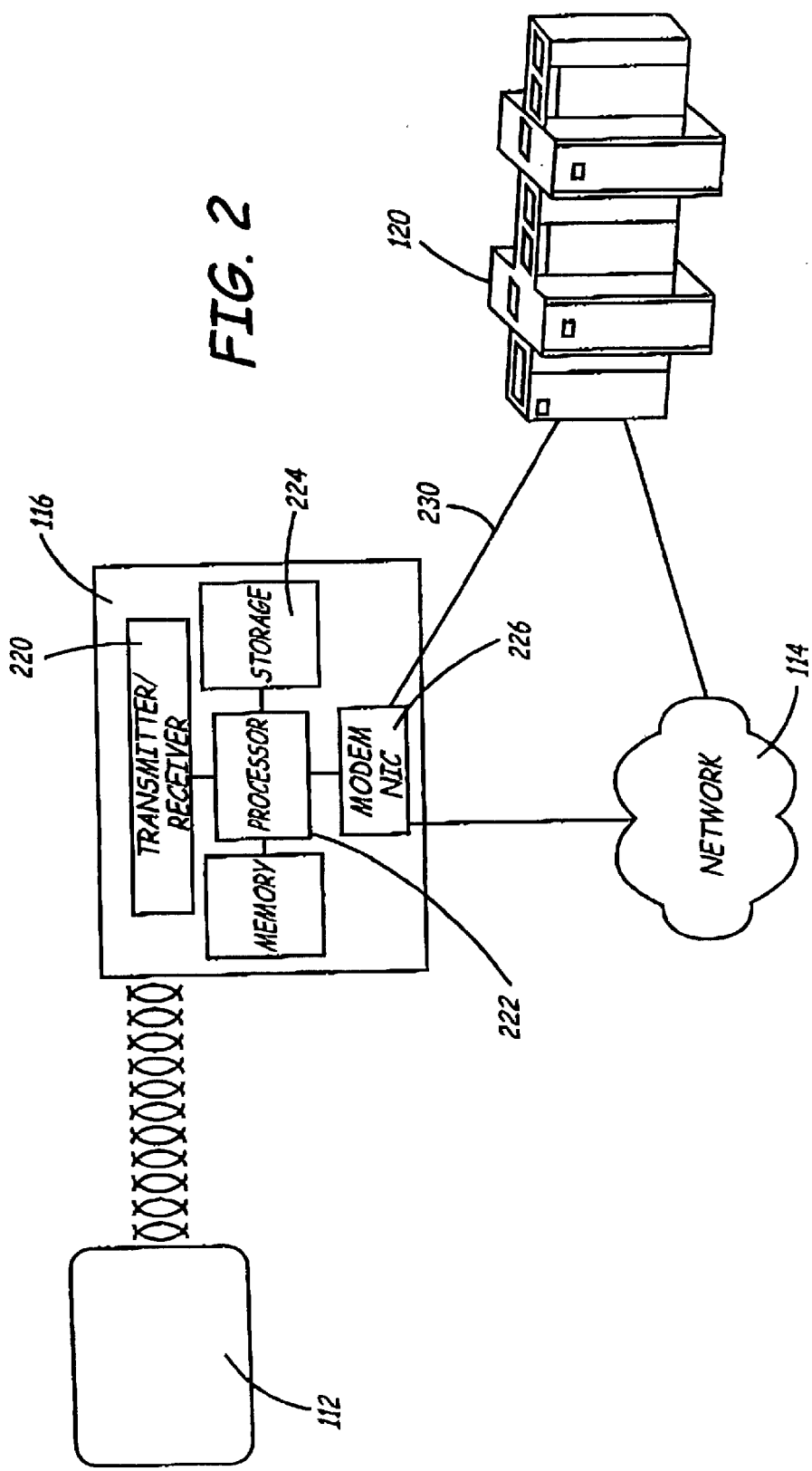

INSTRUMENTATION AND SOFTWARE FOR REMOTE MONITORING AND PROGRAMMING OF IMPLANTABLE MEDICAL DEVICES (IMDS)

This application claims the benefit of U.S. Provisional Application Ser. No. 60/173,080 filed Dec. 24, 1999. The specification and drawings of the provisional application are specifically are incorporated by reference herein.

FIELD OF THE INVENTION

The present invention generally relates to implantable medical devices (IMDs). Specifically, the invention relates to a system providing real-time communication between the IMDs, medical instruments associated with or compatible with the IMDs, and a specialized remote expert data center, a central IMD support information network, or other remote collaborators. A display may be provided to allow users, particularly remote users, to track connection status and progress. More specifically, the invention relates to a central network to provide for a easily-accessed connection to the expert data center, central IMD information center, or other remote collaborators to promote reliable real-time connectivity between clinicians, IMDs and related medical devices as well as providing remote monitoring for proactive patient therapy and clinical care. The expert data center may be a web-enabled remote server which stores device registration and patient management data.

BACKGROUND OF THE INVENTION

In the traditional provision of any medical services, including routine check-ups and monitoring, a patient is required to physically present themselves at a provider's office or other clinical setting. In emergency situations, health care providers may travel to a patient's location, typically to provide stabilization during transport to a clinical setting, e.g., an emergency room. In some medical treatment applications, accepted medical practice for many procedures will naturally dictate physical proximity of medical providers and patients. However, the physical transport of patients to various clinical settings requires logistical planning such as transportation, appointments, and dealing with cancellations and other scheduling complications. As a result of such logistical complications, patient compliance and clinician efficiency may suffer. In certain situations, delays caused by patient transport or scheduling may result in attendant delays in detection of medical conditions including life-threatening situations. It is desirable, therefore, to minimize situations in which the physical transport of a patient to a particular clinical setting is required.

After the implantation of an IMD, for example, a cardiac pacemaker, clinician involvement with respect to the IMD has typically only begun. The IMD usually cannot be merely implanted and forgotten, but must be monitored for optimal results, and may require adjustment of certain parameters or settings, or even replacement, in response to or in anticipation of changes in patient condition or other environmental factors, or based on factors internal to the device. IMDs may also contain logic devices such as digital controllers, which may need to undergo firmware or software upgrades or modifications. In addition, information about the IMD may be gathered for treatment or research purposes. For example, many IMDs are capable of storing certain state information or other data regarding their operation internally.

Because IMD operation and patient physiology is preferably monitored to help effect the desired patient outcome, it would be desirable if data collected by an IMD could be viewed and administered remotely. Similarly, it would also be desirable that the instructions installed in an IMD may be modified in response to patient physiologic information, or perhaps be upgraded remotely as well.

In the event a change, modification or reprogramming of the IMDs is indicated, it would be desirable if the instruction could be implemented in the IMD as soon as possible, thus providing more continuous monitoring to proactively effect changes in the IMDs for efficient therapy and clinical care. This scenario may be contrasted with a reactive practice of responding to an adverse patient event or subjecting the patient to the inconvenience or expense of frequent in-person encounters with a clinician, for example after an unexpected therapy by the device, or to effect other monitoring of device functioning, e.g., spontaneous therapies by the device. For example, an implanted cardioverter defibrillator may administer to the host patient a cardioversion or defibrillation therapy. After such therapy, it is typically desirable to determine the parameters of, for example, an arrhythmia that a therapy was administered in response to, or of the therapy administered.

Prior art methods of clinical services, particularly IMD monitoring and adjustment, are generally limited to in-hospital procedures or other scenarios involving patient transportation to a clinical setting. For example, if a physician needs to review the performance parameters of an IMD in a patient, it is likely that the patient has to go to the clinic. Further, if the medical conditions of a patient with an IMD warrant a continuous monitoring or adjustment of the device, the patient would have to stay in a hospital indefinitely. Such a continued treatment plan poses both economic and social problems. Under the prior art, as the segment of the population with IMDs increases, many more hospitals and clinics, and attendant clinicians and service personnel will be needed to provide in-hospital service for the patients, thus escalating the cost of healthcare. Additionally, the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to download the stored data from the IMD. Depending on the frequency of data collection, this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed.

In addition to the patient concerns described above, the implantation and ongoing administration of a medical device must be carefully documented or recorded by various clinicians and commercial entities. For example, a clinician may wish to record information about the device such as its serial and model number in order to inform the patient of any firmware or software updates or upgrades involving the device, and to issue reminders to the patient regarding significant dates involving the IMD in order to generally aid in patient compliance. The IMD may also have a regular maintenance period suggested or prescribed, for example, for renewal of a power supply or refill of a reservoir containing a drug administered by the device. Similarly, the manufacturer and/or seller of the device will probably wish to record information about the device such as its serial and model number, manufacturing date, its batch or lot, the patient receiving the implant, the clinical entity administering the device, and the like, in order to ensure than any important information that may involve the device may be promptly provided to the patient either directly or indirectly. In addition, the manufacturer may be engaged in demographic or cohort clinical studies or data collection regarding etiological and device outcome scenarios across a population receiving a certain medical device or general category of medical device. Furthermore, the manufacture may wish to track demand of various product lines in order to determine which products or types of products are subject to greater demand, and accordingly should receive a greater investment of health care research and supply funds. In particular, the manufacturer will wish to maximize the likelihood that an implantable medical device will be available to a patient that needs one.

In general, then, the administration of an IMD may require ongoing involvement by various clinicians and medical personnel, the decisions and input of whom may materially affect the decisions that the other involved clinicians make on an ongoing basis. Accordingly, collaboration between these clinicians and coordination of their various treatment decisions and prescriptions is desirable. However, the mobile nature of the modern medical professional's practice is well-known. A single physician, for example, may be affiliated with multiple different hospitals, offices, and other clinical settings, as well as with various corporate and professional entities. In addition, the typical clinician's busy schedule often makes it difficult if not impossible to predict where he or she may be reached at a particular time. The profession's relatively early deployment of pager technology is demonstrative of the highly mobile character of medical practice. Further complicating the ability of clinicians to communicate with each other is the fact that they are frequently involved in medical procedures where interruptions are, at best, inconvenient. In general, a medical professional may have multiple and unpredictable phone numbers leading to uncertainty as to where they can be reached, particularly with regard to wired telephone devices presently most suitable for reliable data transfer.

Advancements in IMD and related technologies have made it possible to effect certain IMD administration telephonically, i.e. effecting data communications over Plain Old Telephone Service. For example, IMDs may be telephonically connected with remote devices that may need to send or receive information with respect to the IMD. However, maintaining an address book on a medical instrument requires a significant time investment for the user to enter contact information. Further, each contact may have multiple and unpredictable telephone numbers depending on the clinicians' location at any given time. If users must enter or dial telephone numbers in order to communicate with remote medical devices, it complicates their goal of conducting a collaborative patient session with the remote medical instrument. Furthermore, if a central data repository must be accessed in connection with IMD administration, a clinician or technician is presently required to dial one number for data transfer to the central data repository network, and one or more other numbers for collaboration with remote medical devices.

In general, the number of people having implanted medical devices has been increasing over the last few years, with an attendant increase in operator personnel. The total effect of these phenomenon is a widely dispersed and large body of operators. Thus, it is desirable to have a high efficiency communications system that would enhance data communications, both between the IMDs and medical instruments, such as programmers; between operators and entities providing IMD updates and education such as manufacturers, and between clinicians and medical professionals administering IMDs. In a preferred embodiment of the present invention, the centralized collaborative network supports chat, bulletin board, or peer-to-peer instant messaging utilities, in addition to contact and scheduling administration.

In addition to providing an efficient communications network, efficiency would be increased even more if it became possible to limit the degree to which human and particularly clinician involvement is required to effect the communication between an IMD and a remote resource, and to limit clinician, technician, or other human involvement where appropriate in certain aspects of IMD deployment within a patient, once the IMD is implanted. For example, after implantation, the device implanted must be registered. This registration may be linked to the device's host patient, or may be anonymous.

Further, it may be preferred to have an operable communication between the various implants to provide a coordinated clinical therapy to the patient. Thus, there is a need to monitor the IMDs and the programmer on a regular, if not a continuous, basis to ensure optimal patient care. In the absence of other alternatives, this imposes a great burden on the patient if a hospital or clinic is the only center where the necessary upgrade, follow up, evaluation and adjustment of the IMDs could be made. Further, even if feasible, the situation would require the establishment of multiple service areas or clinic centers to support the burgeoning number of multi-implant patients worldwide.

Specifically, the communication scheme should be tailored to enable real-time communication between the remote data center, the programmer or an interface medical unit and the IMDs. The present invention provides a central network or "switchboard" to facilitate remote connectivity of programmers, IMDs and a preferably web-based expert data/management center to dispense real-time therapy and clinical care to patients worldwide.

SUMMARY OF THE INVENTION

According to a representative embodiment of the present invention, a centralized data network is provided with a static "location" which may be accessed by clinicians that are coordinating IMD administration between various remote medical devices and human clinicians. The static "location", which may be, for example, a telephone number or dedicated IP address, may be hard-coded into software or firmware of various medical devices, allowing network access according to this static location. The centralized network that may be accessed at this location may keep track of dynamic locations and addresses of both devices and humans that may wish to access the network or interact with each other. For example, in a representative embodiment of the present invention, a medical device capable of interfacing with an IMD through telemetry may be supplied with an interface which may provide for access to the central network. Data about the patient stored on this network may be accessed, aiding in the administration of the patient encounter. In addition, other clinicians may be communicated with, for example clinicians also accessing the network at the same time. The medical device interfacing with the IMD may also have, for example, a keyboard and monitor or a voice communication device such as a speakerphone or comparable telecommunications device for voice collaboration.

The central network will preferably be "aware" of, or track on a continuous basis all remote medical devices and human clinicians and personnel that are in communication with the central network at any given time. For example, a clinician administering the IMD interface device may consult with a physician at a remote location. This remote physician may have dialed up the central network, or may be connected to the central network via a data communications protocol, e.g. SMTP operating over a public network such as the Internet. The various connections between the remote devices and personnel may be effected as network connections, dial-up data communications connections, direct connections over dedicated lines, voice transmissions over plain old telephone service (POTS), or packetized or other digital voice transmission over data lines, e.g., voice over IP.

In a preferred embodiment of the present invention, if a person or device is not in communication with the central network at a given time, and contact with the person or device is requested by a person or device in contact with the network, the central network will have stored information allowing it to make an educated prediction about where the device or human remote resource may be found, according to, for example, telephone number or IP address.

In a preferred embodiment of the subject invention, one or more buttons or a similarly simple interface may be provided on an electronic medical instrument that will effect a communication link between the medical instrument and a remote central network. Through this remote network, further communications links may be established between the medical instrument on the one hand, and various remote medical instruments, devices, and clinical personnel on the other. These links may be direct links, but are preferably indirect links routed through the central network. In either case, the communications links between devices, or between devices and personnel, provide an interface for the exercise of remote collaboration. For example, a remote medical device having the capability to receive and analyze data from a particular IMD, may be reached via the central network, and be consulted by a clinician in proximity to the IMD. It will preferably not be necessary for the clinician to, for example, know or have access to a telephone number, IP address, or other contact point at which the remote device may be accessed. In addition to eliminating the need for clinicians to use an "address book" or similar application to keep track of remote contact information, the present invention also prevents problems with misdialing or transcription errors with telephone numbers. In a preferred embodiment of the subject invention, the resultant direct or indirect communications link can be used to establish both data transfer, and human real-time voice collaboration. The present invention also provides a central meeting point that clinicians may arrange to interact over at a certain time, without regard to their respective locations. Furthermore, the meeting time may be arranged by postings to the central network that may be accessed by interested or authorized parties.

In one embodiment of the present invention, a groupware system is provided allowing clinicians to make a connection to another instrument or computer for collaboration purposes, or to the network for data transmission purposes. The present invention may be implemented by, for example, supplying medical instruments with remote collaboration and data transfer capability with a hardware button or software control that is labeled to indicate it will make the connection with another instrument or the central collaboration network.

For example, the button may be implemented as an actual physical pushbutton, or as a GUI element "button" on a computer or device monitor that is labeled with the particular instrument or network that the button will effect a connection with, and may be "pressed" by clicking on the GUI button with the computer cursor or touch screen. Regardless of whether the button is implemented in software or in hardware, in describing the invention, the interface to effect the connection may be referred to generally as a "button."

According to an embodiment of the present invention, medical instruments are further provided with a display that allows the user to observe that a connection to the electronic switchboard has been made, and to make a choice to either transfer data, wait for a collaboration partner to sign on, or choose a collaboration partner from those currently on-line. This display may, for example, be implemented as a local computer monitor connected to the medical device, or may be a hardware component of the medical device. A medical instrument configured to implement the present invention will have the ability to establish and maintain a connection, for example, via telephone line or data network to the central data network. In a preferred embodiment of the subject invention, the central data repository electronic switchboard maintains a connection with each logged-on instrument, and routes each instrument to either the network server for data transfer, or to another instrument that is on-line as chosen by the user. The central data repository network will preferably represent each on-line instrument to other instruments with a unique identifier. This may be, for example, a name, a device serial number, an avatar, i.e. a pictorial or other schematic representation of the device, or another suitable unique identifier. Users and operators of medical instruments and devices may select other medical devices connected to the network by means of this unique identifier. The network may provide various remote users and medical devices and/or their operators with a menu or list of all medical devices which may be accessed, according to their unique identification.

An embodiment of the present invention provides for a central data repository that provides on-line networked collaboration partners that may be accessed by, for example, users of medical devices. These collaboration partners, in turn, may also be medical devices, or may be human clinicians or computer resources accessible to the medical device seeking collaboration. For example, the central data network could provide collaboration partners that are on-line at all times. Alternatively, the central data network may present to a remote user the potential collaborators that are on-line at the present time. In this way, the current invention may provide an "instant messaging" service between and among subscribers, members, or users connected to the network; alternatively, the network may provide a multi-user collaboration session comparable to a "chat room" utility.

In this way, the present invention provides a system for directing and facilitating central collaboration of IMDs implanted in patients, even when the patients are in a location remote from necessary equipment or the clinicians trained in operating the equipment. In one embodiment, the invention may be used to reduce or eliminate the need for a clinician or other person available to administer device administration. The invention may also create a means for gathering device data in advance of its actual review of a clinician. In this embodiment of the invention, a computer remote to the host patient may initiate and subsequently store the contents of IMD device memory uploaded and transmitted to the remote computer. This data would then be available for examination in the future. For example, a referring physician could use the ability to examine the patient remotely as a consultation system.

In one embodiment of the present invention, a programmer unit or other interface medical unit that would connect to the centralized data network and repository may be provided. This central repository may be termed, for example, a remote data center. This remote data center will preferably provide access to an expert system allowing for downloading of upgrade data or other expert medical or device information to a local, i.e., IMD or communications device environment. Further, the invention may be implemented, for example, as an integrated software system for efficient voice and data communications to transfer information between the IMDs and a remote expert data center for dispensation of therapy and clinical care on a real-time basis.

Further, in one embodiment of the present invention, it is possible to enable the gathering of high resolution diagnostic/physiologic data, and to transfer information between the IMDs and a remote data center to dispense therapy and clinical care on a real-time basis. Further, the data system contemplated by the present invention enables an efficient system for data storage, collection and processing to effect changes in control algorithms of the IMDs and associated medical units to promote real-time therapy and clinical care.

The proliferation of patients with multi-implant medical devices worldwide has made it imperative to provide remote services to the IMDs and timely clinical care to the patient. The use of programmers and related interface devices to communicate with the IMDs and provide various remote services has become an important aspect of patient care. In addition to the instant invention, the use of programmers may be implemented in a manner consistent with the co-pending applications detailed in the foregoing Cross Reference to Related Applications, and assigned to the assignee of the instant invention. In light of the disclosures of these incorporated references, the present invention provides a vital system and method of delivering efficient therapy and clinical care to the patient.

In a representative embodiment of the instant invention, one or more IMDs, such as a pacemaker, defibrillator, drug pump, neurological stimulator, physiological signal recorder may be deployed in a patient. This IMD may be equipped with a radio frequency transmitter or receiver, or an alternate wireless communication telemetry technique or media which may travel through human tissue. For example, the IMD may contain a transmission device capable of transmitting through human tissue such as radio frequency telemetry, acoustic telemetry, or a transmission technique that uses patient tissue as a transmission medium. Alternately, an IMD may be deployed in a fashion by which a transmission or receiving device is visible externally to the patient but is connected directly or via wires to the IMD. An external device, which may generally be termed an interface medical device or interface medical unit, may be positioned outside the patient, the interface medical device being equipped with a radio frequency or other communication means compatible with the communication media of the IMD or the IMD transmitter/receiver, which may be external to the IMD and may further be external to the patient. Communication may be effected between the IMD transmitter/receiver and the external interface medical device, e.g. via radio frequency. The interface medical device may be connected via a wireless or physical communication media, e.g. via modem and direct dial connection, with the central expert computer or network. In an alternate embodiment of the subject invention, the interface medical device may have a direct connection or tunneled connection directly to the central network. In yet another alternate embodiment of the subject invention, the system may be implemented as a data network that allows the interface medical device access to the central expert network and various distributed devices from many locations, for example providing for an interface medical device that is portable.

The amount of historical data, particularly patient-specific historical data used as input to control systems can be virtually unlimited when it is stored externally to the patient. Furthermore, a more thorough comparison can be made between patients with similar diseases as data and therapy direction are centralized, which may be expected to result in gains to the body of medical knowledge and treatment efficacy. Data from other medical systems, either implanted or external, such as etiological databases, can be incorporated easily into the central expert system. Other anonymous patient experiences or treatment data may be more quickly incorporated into a subject patient's IMD regime than might be possible with existing systems of IMD programming or upgrading. In addition, a subject patient's own historical treatment parameters and corresponding outcomes may be used in making IMD programming and other treatment decisions. In general, the instant invention provides IMD clinicians engaged in collaboration with access to virtually unlimited computing power as part of their data collection and therapy calculation processes.

A collaboration system according to the present invention provides the ability to have high power computing systems interact with implanted medical devices, thus providing the ability to use complex control algorithms and models in implanted medical devices. In addition, even with relatively simple modeling, or in stochastic models, relatively large amounts of historical data from a single or multiple medical devices may be brought to bear for predictive purposes in evaluating alternate therapy and IMD instruction prescriptions. The present invention provides a system that establishes an external communications device and data network as a 'data bus' for extending the processing power of deployed IMDs, while minimizing host patient and clinician inconvenience by allowing remote collaborators.

The present invention may be effected, in part, by the provision of an interface medical device, which may be a standalone device or a computer peripheral device, that is capable of connecting an IMD, or simply data telemetrically received from an IMD, to a central network or other data communication link. While the interface between a computer data link and an implanted medical device is referred to generally herein as a "interface medical device", or the like, it will be appreciated to those skilled in the art that the interface may serve as an interface to a variety of data communications systems, including not only networks, but also, without limitation, direct dial-up connections, dedicated lines, direct satellite links, and other non-network data communications connections.

In one embodiment of the invention, the information network may be established or operated according to any network protocol, for example, TCP/IP over the Internet. The uploading to a central collaboration computer may also be effected over a direct dial-up connection or a dedicated line. Upon uploading of the data, a medical professional or other clinician may be alerted to the fact the data has been uploaded. This clinician may then view the data, if desired.

In an alternate embodiment of the invention, for example, a host patient may effect a dial-up connection to the central data network. In addition to evaluation of device function during routine situations, according to this embodiment of the present invention, a home monitoring instrument may be provided to a host patient allowing the patient to send data, i.e., to effect central collaboration, if, for example, they have a subjective belief that they are symptomatic. For example, a host patient of a cardioverter defibrillator IMD may effect central collaboration if they believe they have suffered an arrhythmia event. The data resulting from the central collaboration may then be made remotely accessible for evaluation by a pacing system expert. In a preferred embodiment of the subject invention, IMD function data and physiologic data of the host patient is made available nearly instantaneously to a clinician capable of evaluating the device function, physiologic event or data, or therapy administered by the target IMD.

In a preferred embodiment, the central collaboration network of the present invention is implemented as a software application which may be run on a server or central computer accessible via a network or direct connection by the interface medical device. In an alternate embodiment, the interface medical device may be implemented as a software client which may run on a computer remotely from the collaboration server. Preferably, the central collaboration computer, program or device is capable of autonomously and dynamically determining the model of an IMD, for example, according to manufacturer, type, and model number, as well as the specific serial number of a particular device. When an IMD is within communication range of an interface medical device, the central collaboration computer of the present invention is also preferably capable of configuring a deployed IMD, or commanding the interface medical device to retrieve data from the IMD.

In a representative embodiment, a session according to the present invention may proceed according to the following scenario. In order to begin a collaboration session, a host patient will typically present to an interface medical device, possibly aided by a clinician or technician. For example, the patient may place themselves in the vicinity of the interface medical device within range of the telemetry capacities of the interface medical device. This may take place, for example, at a medical facility such as an Emergency Room, Follow-up Clinic or Operating Room. At the initiation of a session, it will be preferable to configure the target IMD for optimal operation for central collaboration. For example, the interface medical device may be programmed to issue a command to the target IMD to "Cancel Magnet", "Resume Therapy," or another command to enter a mode consistent with the collaboration process. Either prior to or after the establishment of a telemetry or other communication link with the target IMD, the interface medical device operator will effect a communications link between the interface medical device and the central collaboration network expert computer. This interface medical device operator may be a human attendant or technician, an automated module of the interface medical device firmware or software, or may be implemented as a software application on a general purpose computer connected to the interface medical device. Alternatively, the remote central expert computer may lead a human or automated interface medical device central expert computer through the steps of establishing a telemetry interface between the IMD and interface medical device; with the interface medical device in turn notifying the central collaboration computer when a telemetry connection has been established. Communication with the central collaboration network server may be established via a network connection, such as a LAN or WAN. In this embodiment of the present invention in which the interface medical device is preferably attended by an operator, the operator may be the host patient of the target IMD, or it may be attendant personnel at a clinical setting. In either case, the operator may connect the interface medical device to a suitable network connection, if a network connection is not already in place. For example, a direct dial-up connection may be established in this manner by physically connecting the interface medical device into a telephone connection jack such as a RJ-11 analog jack. The operator at some point would turn the interface medical device on and instruct the interface medical device system to establish communications with a pre-configured telephone number, IP address, or other communication location.

In a preferred embodiment, the central collaboration network and expert system of the present invention is implemented as a software application which may be run on a server or central computer accessible via a network or direct connection by the interface device. In an alternate embodiment, the programmer may be implemented in part as a software client which may run on a computer remotely from the server. Preferably, either the interface medical unit or the central expert center is capable of autonomously and dynamically determining the model of an IMD, for example, according to manufacturer, type, and model number, as well as the specific serial number of a particular device. When an IMD is within communication range of an interface medical device, it is also preferably capable of configuring the deployed IMD, or commanding the interface medical unit to retrieve data from the IMD.

BRIEF DESCRIPTION OF THE DRAWINGS

FIG. 2 depicts the hardware architecture of a device according to the present invention and its operation within the network of FIG. 1.

DETAILED DESCRIPTION OF THE DRAWINGS

Figure 1:
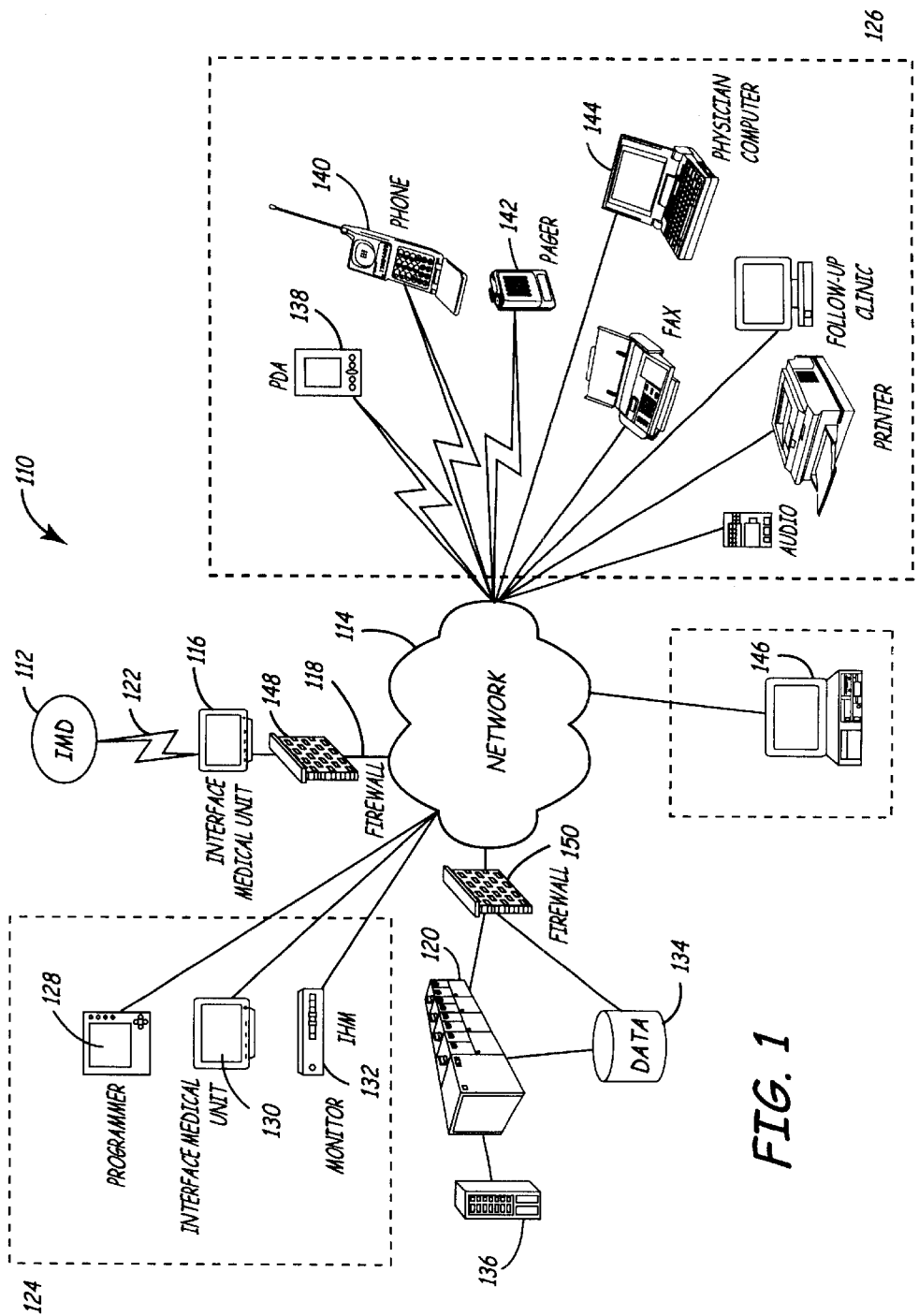
FIG. 1 depicts a general network architecture diagram of a system embodying the subject invention.

FIG. 1 depicts a general network architectural view of a central collaboration network according to an embodiment of the present invention. An IMD collaboration network system 110 is depicted. IMD 112 has been deployed in a patient, for example, a patient at a location remote from central collaboration network 114. The IMD 112 may be one of a number of existing or to be developed IMDs, for example, a pacemaker, defibrillator, drug pump, neurological stimulator, physiological signal recorder, oxygen sensor, or the like. A device external to the patient is provided which may be termed generally an interface medical device 116. This networked interface medical device 116 may communicate with the IMD 112 via, e.g., radio frequency. The interface medical device 116 may also communicate with a central collaborative network 114 via modem, LAN, WAN, wireless or infrared means according to network connection 118. This central collaborative network 114 is preferably able to communicate via a computer network or other suitable data communications connection with a central computer 120 in communication with central collaborative network 114. While in FIG. 1, a single IMD 112 is depicted, the subject invention permits of use with multiple IMDs deployed in a single patient, each making separate transmissions and receiving separate instructions from interface medical device 116. In an alternate embodiment of the subject invention, multiple IMDs deployed in a single patient are all linked to a single telemetry device implanted in a patient. This telemetry device may be separate from or incorporated into one of the IMDs deployed in a patient.

Returning to the single IMD embodiment depicted in FIG. 1, IMD 112 is equipped with or linked to a transmission and receiving device such as a radio frequency telemetry device, also preferably implanted in a patient. The central collaborative network 114 computing center or central computer 120 preferably has sufficient computing power and storage capability to collect and process large amounts of data with regard to user, device and clinician location and scheduling. The patient is placed or places himself or herself in proximity to interface medical device 116. For example, interface medical device 116 may be placed in a patient's home, at their bedside perhaps, or may be placed in a community center, clinical office setting, nursing home, or other care facility. Interface medical device 116 may also be embodied in a portable device that may be carried by the patient, or by a clinician. Interface medical device 116, like IMD 112, contains or is linked to a communications media transmitter/receiver compatible with the type incorporated into or linked to IMD 112. In an illustrative embodiment of the subject invention, interface medical device 116 contains a radio frequency transmitter/receiver or similar radio frequency telemetry device establishing radio frequency link 122.

Various medical devices 124 and telecommunications and data communications devices 126 are preferably available through central collaborative network 114. This central collaborative network 114 may be a public network, such as the Internet. For example, via central collaborative network 114, remote medical devices such as programmer 128, interface medical unit 130, or remote monitor 132 may be accessed. In one embodiment of the subject invention, these remote medical devices 124 may be accessed using a simple software or hardware interface button which automatically connects local interface medical unit 116 to a remote medical device 124 via central collaborative network 114. For example, the IP address, IPv6 address, or other network node or location, or dial-up telephone number of remote medical device 124 may be hard-coded or otherwise programmed into interface unit 116, and selected quickly from a list of available medical devices 124, or, for example, from a sublist of available medical devices, the sublist made up of remote medical devices that the interface units has collaborated with in the past.

In a preferred embodiment of the subject invention, rather than hard-coding a static address or phone number for remote medical device 124 into interface medical unit 116, a static identifier for one or more remote medical devices may be coded or programmed into interface unit 116. This identifier is preferably unique within collaborative network 114, but need not be unique among the entire world or among devices with access to a public network 114. For example, if central collaboration network 114 is implemented using the Internet, it is preferably not necessary to have each remote medical device 124 have a separate unique IP address coded into interface unit 116. Instead, the interface unit 116 identifies a target remote medical device 124 using an identifier that is unique within the system of the present invention. For example, the remote medical device 124 may be identified by a serial number, unique key name, or avatar visible on interface unit screen 116. Upon transmission of the unique identifier of the target remote medical device 116, the target device transmission information is preferably forwarded over central collaboration network 114 to central computer 120. This central collaboration computer 120 will preferably be possessed of appreciably more computing power than possible with an IMD 112, in terms of processor speed, RAM available, and other data storage. Central collaboration computer 120 is large scale in comparison to such processors that are available for incorporation into an IMD 112. For example, some commercially-available personal computers may contain sufficient computing power to operate as a server capable of carrying out some collaboration tasks of the present invention. In a preferred embodiment of the subject invention, however, central collaboration computer 120 will be a mainframe, multi-processor supercomputer, or a multi-processor workstation, such as a type available from Silicon Graphics, Inc./SGI of Mountain View, Calif. Such relatively high-powered computing devices may be better suited to efficient routing and posting of collaborative communications.

Regardless of which computing device is used, in accordance with the present invention, the computing device will be configured as a server capable of communicating directly or indirectly with interface medical device 116. The central collaboration computer 120 will preferably have sufficient storage, either internal to the computer or linked to the computer as depicted in storage device 134 for the storage of massive amounts of clinician and device contact information, and of historical patient data from, for example, a particular patient having an IMD 112 in communication with central collaboration computer 120. Data storage element 134 may contain any suitable means of data storage, including but not limited to hard drive, or another readable/writable magnetic or optical storage. In a preferred embodiment of the subject invention, data storage element 134 has a redundant array of disks such as a redundant array of inexpensive disks (RAID) system. Preferably, central computer 120 has relatively direct access to data storage facility 134. On data storage facility 134, the various "real-world" locations, node points, network addresses, phone numbers, or other unique network and/or telecommunications nodes, addresses, locations, or phone numbers are stored for access by central computer 120. The stored telecommunications network location information may be stored according to any suitable data storage or database scheme to facilitate low-overhead and prompt selection of the real-world network node. For example, the unique system identifier attributed to a particular medical device 124 and corresponding network or telecommunications address, node or number may be stored in a linked list, tree, hash table, dual linked list, or other lookup table or suitable data structure or database scheme. The network location of remote medical device 124 may also be stored on expert/data server 136 in addition to or instead of data storage facility 134.

In addition to remote medical devices 124, interface medical unit 116 may also effect interfacing or collaborative communications sessions with telecommunications or data communications devices 126. These may include, without limitation, personal digital assistant (PDA) 138, cellular or wired telephone 140, pager 142, or remote clinician computer 144. Like remote medical devices 124, the network location, network address, dial-up phone number, or other nodal or location information of communications devices 126, are preferably stored in data storage media 134 in order to be accessed by central collaboration computer 120. Because some collaboration that users with to effect over collaboration network 114 may be voice communication, collaboration network 114 and central collaboration computer 120 are capable of transmitting and routing voice communications, e.g., voice communication data packetized and transmitted using the TCP/IP protocol (voice over IP). In some cases, direct dial-up voice communication over Plain Old Telephone Service may be effected or facilitated using the central location and availability logging of central collaboration computer 120 together with automated dialing by central collaboration computer 120.

A third type of remote unit that may be accessed via central collaborative network 114 is remote computer 146. This remote computer 146 may implement the functions of a medical device, such as remote medical devices 124. Alternatively, remote computer 146 may be used by a human clinician to instruct or interact with interface unit 116, for example, instructing interface unit 116 to send instructions downloaded from remote expert server 136 to remote IMD 112. Remote computer 146 may display information not only from central collaboration computer 120, but also from remote medical devices 124. A clinician using remote computer 146 may also carry out interactive collaboration or "chat" sessions with other clinicians in order to discuss one or more possible clinical procedures or IMD programming strategies being considered, for example. These collaborative sessions may be carried out between a clinician on remote computer 146 and other clinicians using other remote computers 144 or 146 that may communicate with other remote computers 146 over collaborative network 114. Individual clinicians may log-in or register with central collaborative computer 120 in order to indicate their accessibility through the network at a certain place which may be monitored or logged by central collaboration computer 120. The clinician may be identified on the network by a unique identifier such as a user name. As an alternative to client interactions, and for scenarios in which not all interested participants may be on-line or otherwise available at one time, central collaboration computer 120 also preferably supports a "bulletin board" USENET groups, or newsgroups service, e.g., using NNTP.

In a preferred embodiment, an interaction between a deployed IMD 112 and an interface medical unit 116 may take place within a discrete session. This session may encompass collaboration of one or more IMDs deployed in a single patient. A session according to the present invention may proceed according to the following scenario. In order to begin a device collaboration session, a host patient will typically present to an interface medical unit 116. For example, the patient may place themselves in the vicinity of the interface medical unit 116 within range of the telemetry capacities of the interface medical unit 116. For example, this may take place at a medical facility or clinical setting such as an Emergency Room, Follow-up Clinic or Operating Room. At the initiation of a session, it will be preferable to configure the target IMD 112 for optimal operation for central collaboration. For example, the interface medical unit 116 may be programmed to issue a command to the target IMD 112 to "Cancel Magnet", "Resume Therapy," or another command to enter a mode consistent with the collaboration process.

Either prior to or after the establishment of a telemetry or other communication link with the target IMD 112, an interface medical unit 116 Operator will effect a communications link between the interface medical unit 116 and the central network 114. This interface medical unit 116 Operator may be a human attendant or technician, but preferably will be an automated module of the interface medical unit 116 firmware or software, or may be implemented as a software application on a general purpose computer connected to the interface medical unit 116. Alternatively, the central collaboration computer 120 may lead a human or automated programmer operator through the steps of establishing a telemetry interface between the IMD 112 and interface medical unit 116 with the interface medical unit 116 in turn notifying the central collaboration computer 120 when a telemetry connection has been established.

Communication with the central collaboration network computer 120 or expert server 136 may be established via a network connection, such as a LAN or WAN or over a public network 114. In this embodiment of the present invention in which the programmer is preferably attended by an operator, the operator may be the host patient of the target IMD, or it may be attendant personnel at a clinical setting. In either case, the operator may connect the interface medical unit 116 to a suitable network connection, if a network connection is not already in place. For example, a direct dial-up connection may be established in this manner by physically connecting the interface medical unit 116 into a telephone connection jack such as a RJ-11 analog jack. The operator at some point would turn the interface medical unit 116 on and cause the interface medical unit 116 to dial a preconfigured telephone number or connect with a preconfigured remote network location medical device 124, or communication device 126, by means of a button or similar simple interface.

FIG. 2 depicts the hardware architecture of a device according to the present invention and its operation within the network of FIG. 1, depicting in greater detail a suitable architecture for interface medical unit 116 of FIG. 1. As shown in FIG. 2, interface medical unit 116 contains a transmitter/receiver 220, a processor 222, storage device 224, and communication device 226. Communication device 226 may be, for example, a modem or network interface card. It may be seen in FIG. 2 that interface medical unit 116 contains architecture components similar to those seen in a general purpose computer, and in an alternate embodiment of the subject invention, the collaborative network 110 of the present invention may be deployed with interface medical unit 116 implemented as a computer with a telemetry peripheral device analogous to interface medical unit element 220 that may communicate with IMD 112.

While interface medical unit 116 is portrayed primarily as a self-contained or stand-alone unit, it will be appreciated that interface medical unit 116 may also be implemented as a peripheral transmitter/receiver capable of wireless communication with IMD 112, and also in communication with a computer such as a personal computer such as a laptop or portable computer. Implemented on a computer, interface medical unit 116 may also be a terminal or client of a remote computer, including of central collaboration computer 120. It will be appreciated that in the event that interface medical unit 116 is implemented as a peripheral and terminal, some of the components of interface medical unit 116, e.g., storage component 224, may be implemented on central collaboration computer 120 or a storage device 134 accessible to central collaboration computer 120 rather than in the terminal implementing interface medical unit 116.

As shown in FIG. 2, communications between interface medical unit 116 and central collaborative computer 120 may be effected either through a collaboration network 114, such as a LAN or the Internet, or communications may be effected through a direct dial-up or dedicated line, or through a terminal connection to a mainframe. These possible implementations are indicated generally by direct communications link 230. Typically, these connections may be considered alternatives; or both communications links, i.e., relatively direct link 230 and link through network 114 may be implemented in order to provide a backup communications system to the link used as the primary communication method.

Security and integrity of the patient information stored on the collaborative computer 120 or storage device 134 and IMD interface operation will preferably be closely guarded for at least the following reasons: First, patient physiologic data detected by a deployed IMD 112 will be transmitted via interface medical unit 116 to central collaboration computer 120 for purposes of analysis of this data, and treatment regimens and/or IMD 112 instructions, firmware, or software may be changed on the basis of this information and collaboration over network 114 as described above. Accordingly, integrity of transmitted data and instructions will preferably be maintained so as to avoid adverse patient outcomes or patient outcomes that do not take full advantage of the subject invention. In addition, patient information that may be linked to an identifiable individual is typically regarded as confidential. Accordingly, encryption or tunneling will preferably be provided to ensure patient confidentiality, particularly when transmissions between interface medical device 116 and central collaboration computer 120, or between central computer 120 and remote devices 124 or 126 takes place though media other than a dedicated line/direct dial-up connection, such as connection 230 in FIG. 2. For example, transmissions may be effected over a packet-based network technology over a public network or internetwork 114. For example, if the transmissions are routed over the Internet using TCP/IP, encryption will preferably be used. As an alternative to encryption, a proprietary data exchange format/interface or scripting language that is kept secret may be used in communications between IMD 112 and central collaboration computer 120. However, even with secure dedicated lines 230 or a secret data format, digital signatures will preferably be used to detect corruption of data. Additional implementations of security systems may also be utilized in accordance with the subject invention, including biometric security apparatus and methods to detect inalterable physical characteristics of persons attempting to access the patient data via remote computer 146 in order to authenticate the would-be user of the system.

Security measures such as the foregoing will preferably be used to authenticate the interface medical device 116 and IMD 112, as well as persons attempting to access patient information, particularly individually identifiable patient information. Accordingly, a preferred embodiment of the subject invention utilizes digital signatures and encryption of the patient information and IMD 112 instructions being transmitted according to the present invention. Encryption of patient information will serve to protect patient confidentiality. Each transmission of patient data will preferably have a digital signature that can be checked against the transmission payload to ensure that patient data and IMD 112 instructions were not corrupted during transmission. Examples of encryption/digital signature schemes that should prove sufficient for suitable encryption of patient information and digital signatures include PGP, the RSA public key infrastructure scheme, or other consumer-level or higher, prime number based encryption signature scheme. Biometric data used to authenticate and verify accessors of the data may include retina scans, iris scans, fingerprint scans, veinprint scans, voiceprints, facial geometry/facial recognition according to facial nodal points, or hand geometry scans.

In addition to the above security implementations, a preferred embodiment of the subject invention incorporates firewall and/or proxy server technology, as indicated in FIG. 1 at firewalls 148 and 150. Such security measures not only protect patient data stored in data storage element 134 from access by unauthorized persons, but also protect interface medical device 116 and IMD 112 from improper snooping and/or improper instruction from negligent or unscrupulous persons that may have access to data network 114.

Transmissions between an IMD 112 and interface medical device 116 or between peripheral physiological data gatherer 232, or other peripheral devices will also preferably be protected from transmission errors using similar encryption, authentication, and verification techniques to those discussed above, and/or wireless communication enhancement techniques such as wireless modulation or another suitable wide-frequency spectra technique. Preferably, encryption and/or authentication will be effected end-to-end, i.e., covering the entire transmission from IMD 112 to central computer 120 or from computer 120 to IMD 112 or remote devices 124 or 126, rather than effecting one encryption/verification scheme between IMD 112 and interface medical device 116, and a different scheme between interface medical device 116 and central computer 120. As an alternative to, or in addition to the above authentication scheme, radio frequency pulse coding, spread spectrum, direct sequence, time-hopping, frequency hopping, a hybrid spread spectrum technique, or other wireless modulation techniques may be employed in order to reduce interference between IMD 112 and other IMD or other wireless devices, and to generally offer improved accuracy, reliability, and security to transmissions between IMD 112 and interface medical device 116, may be used to avoid cross-talk or confusion among IMDs and/or interface medical devices in proximity to each other. For example, radio coding may be implemented to avoid transmission errors or device confusion between neighboring IMD 112 patients utilizing a device implementing aspects of the present invention in a managed-care setting.

Upon establishment of a network connection, or direct dial-up connection, a communications link is established over which the interface medical device 116 may establish a connection with the central collaboration computer 120. Communication over collaboration network 114 may be effected by way of a TCP/IP connection, particularly one using the Internet, as well as a PSTN, DSL, ISON, Cable Modem, LAN, WAN, MAN, direct dial-up connection, a dedicated line, or a dedicated terminal connection to a mainframe. The initial communication may focus on authentication of the interface medical device 116. This will preferably include verification that the interface medical device 116 is certified for interrogating IMDs, i.e., a verification process has established that the software and hardware revisions are current, and that the authentication information uniquely identifies a specific known interface medical device 116.

Further considering the steps in a representative embodiment of the invention in which the interface medical device is attended by an operator, the central collaboration computer 120 may next instruct the interface medical device Operator such as a human user how to configure the telemetry interface 122 between interface medical unit 116 and IMD 112. This would typically be specific for the type of IMD 112 being interrogated and might involve, for example, placing a programming head or wand near the IMD 112, or just positioning the patient and interface medical device 116 in proximity. The interface medical device 116 may then notify the remote collaboration computer 120 that a telemetry connection has been established.

In a representative embodiment of the invention, a device agent software module may be selected from remote expert server 136 to interface with a particular type or model of IMD 112. In an embodiment of the subject invention in which the interface medical unit 116 is configured to dynamically identify an IMD 112 presented to it for establishment of central collaboration, preferably an initial IMD 112 identification stage precedes the selection of device agent module. In an embodiment of the present invention configured or adapted for use with an in-home monitor device, preferably the interface medical device is preconfigured to work only with the specific device(s) implanted in an individual host patient of the residence.

Upon execution of the applicable software module, for example the device agent corresponding to the IMD 112 presented to the interface medical device 116, the central collaboration computer 120 may retrieve certain pertinent data from the interface medical unit 116 and/or IMD 112, including physiologic data regarding the host patient stored in IMD 112 memory, stored power remaining, amount of drug remaining within the device, or hardware, software, or firmware version information, or other device status information.

Upon completion of collaboration, the central collaboration computer 120 may signal the completion of the operation to interface medical device 116. Preferably, the central collaboration computer 116 will then close the connection with interface medical device 116, for example after a disconnect request to the interface medical device 116, for example, as part of the implementation of a symmetric release to avoid possible loss of data. The interface medical device 116 may then terminate the telemetry or other wireless connection with the IMD 112. This may involve the issuance of instructions to a human interface medical device 116 Operator, if applicable, to effect the termination in a certain manner, for example, by removing the interface medical device 116 from proximity to the host patient. Preferably, the interface medical device 116 will not terminate communication with the IMD 112 until after the connection with the central collaboration computer 120 is released.

Various data communications methods may be suitable for transmission of the target device 112 and host patient data to the collaboration network 114 including an SMTP e-mail, FTP, or TCP/IP. In one embodiment of the present invention for example, properly authenticated interested parties may access the patient or device data, the data residing on a server such as the central collaboration computer 120, via TCP/IP protocol using a web browser. As part of the collaboration process, a confirmation that a remote clinician, for example, a clinician that is located somewhere other than the site of the interface medical device 116 data collection point, or from the central collaboration computer 120 has accessed the data via remote computer 146, may be transmitted to the interface medical unit 116 or to another location or device 124 or 126. This confirmation may be effected, for example, by a reply e-mail from a clinician that has received an SMTP message from central collaboration computer 120, indicating that the data has been received or reviewed.

The present invention admits of various scheduling or collaborative efforts. For example, a follow-up collaboration regarding a target device a certain prescribed time following an in-person appointment or other event may be provided for and automatically scheduled for execution by interface medical device 116. For example, the interface medical device 116 may be programmed to poll for or otherwise attempt to establish telemetry or other data communication with a target device 112 at a certain time or interval; the success of the attempt possibly being contingent on the host patient being in proximity to the interface medical device 116 at the specified time, or on the connection of the interface medical device 116 being physically or otherwise connected to a data communications means such as a wireless connection or physical connection such as a RJ-11 phone jack. The present invention also admits of use during or following symptomatic events experienced by a host patient, providing for emergency collaboration. For example, an entity maintaining central collaboration computer 120 and/or collaboration network 114 may provide 24-hour on-call clinical staff for collaboration over, e.g., telephone 140. In any event, more convenient and/or more frequent collaboration and analysis is provided by the present invention, with a reduced reliance on in-person or on-site clinical visits by the host patient. In one embodiment of the present invention, the central collaboration network system described herein may be provided to a host patient or to a clinician or clinical entity on a subscription basis, or on a fee per use or per data access basis.

In a preferred embodiment of the subject invention, collaboration system 110 will operate asynchronously, permitting for the possibility for breaks in the continuous and real-time communications and/or processing of the three subsystems (IMD 112 interface medical device 116, and central collaboration computer 120). However, alternate embodiments of the invention are also possible, including synchronous, "real-time" collaboration regarding the target IMD 112. This alternate "real-time" embodiment of the system 110 may be enhanced upon the establishment of more ubiquitous and robust communications systems or links.

Initially the system would act in an asynchronous manner, where precise timing of data transfer and therapy changes is not critical. As the device-instrument and network communications become more ubiquitous and less reliant on specific hardware (e.g. RF head, network cables), the control loop could become more time-dependent.

Although the invention is described with reference to particular embodiments, it will be understood to those skilled in the art that this embodiment is merely illustrative of the application of the principles of the invention. Numerous modifications may be made therein and other arrangements may be devised without departing from the spirit and scope of the invention.

What is claimed is:

1. A computerized method of automatically obtaining and distributing data from one or more IMDs deployed in one or more patients, comprising the steps of:
    transmitting via a network communication link IMD data pertaining to at least one of the IMDs to an interface device communicating with a central computer system external to any patient;
    routing the IMD data to the central computer system; and
    routing the IMD data to one or more peripheral devices.

2. The computerized method of claim 1, wherein the IMD data comprises physiologic data from the patient.

3. The computerized method of claim 1, wherein the IMD data comprises device information.

4. The computerized method of claim 3, wherein the device information comprises at least one of device model number, serial number, hardware, firmware, or software identification patient name, patient contact information, clinician name, and clinician entity.

5. The method of claim 1, wherein the network communication link comprises a radio frequency link.

6. The method of claim 1, wherein the network communication link comprises a hybrid link.

7. The method of claim 6 wherein the hybrid link comprises a radio frequency link from an IMD to a network interface, and a secondary network link from the network interface to the computer.

8. The method of claim 7 wherein the secondary network link is a direct dial up connection.

9. The method of claim 7 wherein the secondary network link is an area network.

10. The method of claim 7, wherein the secondary network communication link comprises an asynchronous link.

11. The method of claim 7, wherein the secondary network communications link comprises a synchronous link.

12. The method of claim 1 wherein the at least one peripheral device comprises at least one medical device.

13. The method of claim 12 wherein the data pertaining to at least one of the IMDs is data transmitted by a medical device.

14. The method of claim 1 wherein the at least one medical device comprises at least one of a programmer, an interface medical unit, or a monitor.

15. The method of claim 1 wherein the at least one peripheral device comprises a communications device with an interface for humans.

16. The computerized method of claim 1, wherein the one or more peripheral devices comprises at least one selected from the group consisting of a computer, a personal digital assistant, a telephone, a pager, a fax, a printer, or an audio interface.

17. The method of claim 16 wherein the area network is a LAN.

18. The method of claim 16 wherein the area network is a WAN.

19. The system of claim 1, wherein the one or more IMDs comprises one or more of a pacemaker, a PCD pacemaker/cardioverter/defibrillator, an oxygen sensing device, a nerve stimulator, a muscle stimulator, a drug pump, or an implantable monitoring device.

20. The computerized method of claim 1, further comprising the step of storing the data in storage means accessible to the central computer system.

21. The method of claim 1 wherein the data pertaining to at least one of the IMDs is data input by a clinician.

22. The method of claim 21 wherein the data input by a clinician is voice data.

23. The method of claim 21 wherein the data input by a clinician is a bulletin board post.

24. The method of claim 21 wherein the data input by a clinician is a real-time chat forum entry.

25. The method of claim 21 wherein the data input by a clinician is a peer-to-peer instant message.

26. A computerized information network system linking one or more IMD-related medical devices to a centralized computer system via a data communication network, said network comprising:
    a first computer resource accessible by the network, said first computer resource capable of storing data regarding an IMD;
    at least one network interface to at least one medical device, said network interface being capable of communication with the network and with at least one IMD;
    at least one additional peripheral computer in data communication with the first computer.

27. The system of claim 26 further comprising at least one network link with at least one communication device operable by a clinician.

28. The system of claim 27 wherein the at least one communication device is a telecommunications device.

29. The system of claim 28 wherein the telecommunications device is one selected from the group consisting of a telephone, personal digital assistant, a page, or a facsimile machine.

30. The system of claim 26 wherein the communications device is a computer.

31. The computerized network of claim 26, wherein the network comprises a direct link between the at least one network interface and the computer.

32. The computerized network of claim 26, wherein the first computer resource comprises a networked or parallel cluster of processors.

33. The computerized network of claim 26, wherein the data communication is asynchronous.

34. The computerized network of claim 26, where the data communication is synchronous.

35. A computerized method of providing a communication link between an IMD and a remote medical resource, comprising the steps of:
    establishing a first communication path between the IMD and a central repository of medical device contact information;
    selecting a remote medical resource using resource-identifying access data;
    establishing a second communication path to the remote medical resource using the resource access data provided by the central repository.

36. The method of claim 35 wherein the second communication path is implemented as a direct dial-up connection.

37. The method of claim 35 wherein the remote medical resource is a remote human clinician.

38. The method of claim 35 wherein the remote medical resource is a remote medical device.

39. The method of claim 38, wherein the remote medical resource data comprises a unique medical device name.

40. The method of claim 38, wherein the remote medical resource data comprises a unique device serial number.

41. The method of claim 38, wherein the remote medical resource data comprises a unique pictorial representation on a computer monitor.

42. The method of claim 38, wherein the remote device identifier comprises a unique patient identifier.

43. The method of claim 35 wherein the resource-identifying access data is data identifying the IMD.

44. The method of claim 43 wherein the data regarding the IMD is historical physiologic data regarding the patient.

45. The method of claim 43 wherein the data regarding the IMD is a unique IMD identifier.

46. The method of claim 43 wherein the data regarding the IMD is an upgrade to the processor instructions stored within the IMD.

47. The method of claim 35 wherein the second communication path is implemented as an indirect communication path.

48. The method of claim 35 wherein the second communication path is implemented over a computerized data network.

49. The method of claim 35 wherein the second communication path is implemented over telephony links.

50. The method of claim 35 wherein the remote medical resource data comprises a telephone number.

51. The method of claim 35 wherein the remote medical resource data comprises a network or node address.

52. The method of claim 51, wherein the remote medical resource data comprises an IP address.

53. The method of claim 52, wherein the remote medical resource data comprises an IPv6 address.

\* \* \* \* \*